United States Patent [19]

Morita et al.

[11] Patent Number: 5,290,774
[45] Date of Patent: Mar. 1, 1994

[54] PHOTOSTABILIZING METHOD FOR OPHTHALMIC SOLUTIONS AND THE RESULTING OPHTHALMIC SOLUTIONS THEREFROM

[75] Inventors: Takakazu Morita, Toyonaka; Shiro Mita, Ashiya; Yoichi Kawashima, Kyoto, all of Japan

[73] Assignees: Eisai Co., Ltd., Tokyo; Santen Pharmaceutical Co., Ltd., Osaka, both of Japan

[21] Appl. No.: 924,437

[22] Filed: Jul. 31, 1992

Related U.S. Application Data

[63] Continuation of Ser. No. 651,388, filed as PCT/JP90/00950, Jul. 26, 1990, published as WO91/01718, Feb. 21, 1991, abandoned.

[30] Foreign Application Priority Data

Aug. 3, 1989 [JP] Japan .................................. 1-201872

[51] Int. Cl.⁵ ...................... A61K 31/55; A61K 31/27; A61K 31/225
[52] U.S. Cl. .................................... 514/218; 514/480; 514/547; 514/970; 514/972
[58] Field of Search ............... 514/218, 480, 547, 972, 514/970; 424/658, 659

[56] References Cited

U.S. PATENT DOCUMENTS

| | | | |
|---|---|---|---|
| 2,455,366 | 7/1948 | Rigby | 424/659 |
| 3,966,905 | 6/1976 | Nite | 424/80 |
| 4,794,177 | 12/1988 | Corbiere | 514/420 |

FOREIGN PATENT DOCUMENTS 2199745  7/1988  United Kingdom .
WO85/04106  9/1985  World Int. Prop. O. .

OTHER PUBLICATIONS

7126297 Embase No.: 88123613 (1988) Asker et al.
Chemical Abst. 110(6): 141569u (1989) Ogata et al.
Asker et al., "Influence of Certain Additives on the Photostability of Physostigmine Sulfate Solutions", 14(5), 733-746, (1988) Drug Development and Industrial Pharmacy.

*Primary Examiner*—Zohreh A. Fay
*Attorney, Agent, or Firm*—Frishauf, Holtz, Goodman & Woodward

[57] ABSTRACT

This invention relates to a photostabilizing method for ophthalmic solutions and the resulting ophthalmic solutions therefrom. The stabilization is attained by adding polyhydric alcohol and boric acid, and/or sodium borate to ophthalmic solutions which contain a drug substance unstable against light.

19 Claims, No Drawings

PHOTOSTABILIZING METHOD FOR OPHTHALMIC SOLUTIONS AND THE RESULTING OPHTHALMIC SOLUTIONS THEREFROM

This application is a continuation of application Ser. No. 07/651,388, filed as PCT/JP90/00950, Jul. 26, 1990, published as WO91/01718, Feb. 21, 1991, abandoned.

TECHNICAL FIELD

This invention offers a photostabilizing method for ophthalmic solutions, which contain unstable drug substances, against light, and the resulting ophthalmic solutions therefrom.

BACKGROUND ART

There are many drugs which are unstable against light and therefore such drugs are put in practical use by shielding light or by a special pharmaceutical design to prevent decomposition during use.

An aqueous preparation of a drug substance is more easily decomposed by light than a solid form, and the decomposition may cause coloring of the aqueous preparation, etc.

In the case of an aqueous preparation such as an ophthalmic solution, it has so far been difficult to solve the problem of decomposition by light by the pharmaceutical design. Therefore, decomposition has been prevented by shielding light.

However, a complete block of light is practically difficult, and thus we have to revert to the improvement of the formulation to stabilize the solution itself.

Ingredients which can be formulated in ophthalmic solutions are restricted because ophthalmic solutions are administered to the eyes, which are highly sensitive organs. Such restriction causes one of the severe obstacles to design photostable ophthalmic solutions.

DISCLOSURE OF THE INVENTION

This invention offers a photostabilizing method for ophthalmic solutions and the resulting ophthalmic solutions therefrom, which comprises adding polyhydric alcohol and boric acid, and/or sodium borate to ophthalmic solutions containing unstable drug substance against light.

There are various drug substances which are unstable against light, and it is considered that the substances which have aromatic ring substituted by hydroxy, lower alkoxy, primary or secondary amine are generally unstable against light. Examples of such substances are bunazosin, prazosin, terazosin, epinephrine and phenylephrine. Of course, pharmacologically acceptable salts such as a hydrochloric acid salt of a drug substance can be used in this invention.

Polyhydric alcohol is a compound having plural hydroxy groups and is not necessarily restricted to the specific compound. Examples of polyhydric alcohol are glycerol, polyethylene glycol, propylene glycol, mannitol and glucose.

Ophthalmic solutions which contain an unstable drug substance against light are put in practical use by shielding light. However, it is practically difficult to shield light completely, and thus it is desired to stabilize the solution itself by an improvement of the formulation. Ingredients have to be taken into special consideration because ophthalmic solutions are administered to the eyes, which are highly sensitive organs. As the result of our precise study on a photostabilizing method for ophthalmic solutions, we found that photostability of ophthalmic solutions could be attained by adding polyhydric alcohol and boric acid, and/or sodium borate, which have been confirmed as safe additives to ophthalmic solutions. The detailed photostabilizing mechanism of polyhydric alcohol and boric acid, and/or sodium borate is not clear, but it is presumed that the photostability might be attained by conforming a complex with boron and polyhydric alcohol in the aqueous solution. Accordingly, this invention can be widely applied to any drug substances which can conform such complex, and the application should not be restricted to the above-mentioned drug substances. In case of bunazosin hydrochloride, which has a suppressive effect on intraocular pressure, the ophthalmic solutions adding polyhydric alcohol and boric acid, and/or sodium borate were not colored after exposure to an intensive light such as 3000 luxes for 200 hours. On the other hand, the ophthalmic solutions adding only polyhydric alcohol or boric acid were decomposed and colored at the same condition. The details are explained in an article of the stability test. As the result of our study, we found that the photostability of the ophthalmic solutions can be attained by a combination of polyhydric alcohol and boric acid and/or sodium borate, while an addition of boric acid or polyhydric alcohol only is not effective on the photostability.

In this invention, the optimal amount of boric acid or sodium borate is changeable. The amount can be decided according to the nature of the drug substance and the concentration thereof, but the preferable amount is 0.5-2.5 g/100 mL.

The optimal amount of polyhydric alcohol is changeable. The amount can be decided according to the nature of the drug substance and the concentration thereof, but the preferable amount of is 0.1-2.0g/100 mL.

The ophthalmic solutions of this invention can be prepared by the known methods. The outline of the preparative method is that polyhydric alcohol and boric acid, and/or sodium borate are added and dissolved in an aqueous solution of the unstable drug substance against light, and if necessary tonicity agents such as sodium chloride and potassium chloride, stabilizers such as disodium edetate, preservatives such as benzalkonium chloride and pH adjusting agents such as sodium hydroxide and dilute hydrochloric acid can be formulated.

The pH value of the ophthalmic solutions of this invention can be adjusted within a range applicable to medicine and should not be restricted, but the preferable range is 4.5-8.

Examples are shown below.

| [Example] Formulation 1 | |
| --- | --- |
| bunazosin hydrochloride | 0.1 g |
| boric acid | 1.24 g |
| conc. glycerol | 0.3 g |
| benzalkonium chloride | 0.005 g |
| sodium hydroxide | q.s. |
| sterile purified water | q.s. |
| total | 100 ml |

PREPARATION METHOD

Bunazosin hydrochloride, conc. glycerol and benzalkonium chloride were dissolved in sterile purified water and the pH of the solution was adjusted to 6.0. To the solution sterile purified water was added to adjust the total volume to 100 ml.

The following ophthalmic solutions were prepared by a similar method as the above.

Formulation 2

| bunazosin hydrochloride | 0.1 g |
| boric acid | 1.0 g |
| conc. glycerol | 0.5 g |
| benzalkonium chloride | 0.005 g |
| sodium chloride | 0.23 g |
| sodium hydroxide | q.s. |
| sterile purified water | q.s. |
| total | 100 ml (pH 6.0) |

Formulation 3

| bunazosin hydrochloride | 0.01 g |
| boric acid | 1.24 g |
| mannitol | 0.6 g |
| benzalkonium chloride | 0.005 g |
| sodium hydroxide | q.s. |
| sterile purified water | q.s. |
| total | 100 ml (pH 6.0) |

Formulation 4

| bunazosin hydrochloride | 0.1 g |
| boric acid | 1.4 g |
| mannitol | 0.5 g |
| benzalkonium chloride | 0.005 g |
| sodium hydroxide | q.s. |
| sterile purified water | q.s. |
| total | 100 ml (pH 6.0) |

Formulation 5

| epinephrine bitartrate | 2.0 g |
| sodium borate | 2.5 g |
| polyethylene glycol | 0.9 g |
| benzalkonium chloride | 0.005 g |
| sodium edetate | 0.01 g |
| dilute hydrochloric acid | q.s. |
| sterile purified water | q.s. |
| total | 100 ml (pH 7.5) |

Formulation 6

| prazosin hydrochloride | 0.05 g |
| boric acid | 1.0 g |
| conc. glycerol | 0.5 g |
| benzalkonium chloride | 0.005 g |
| sodium hydroxide | q.s. |
| sterile purified water | q.s. |
| total | 100 ml (pH 6.0) |

Formulation 7

| bunazosin hydrochloride | 0.01 g |
| boric acid | 2.0 g |
| propylene glycol | 0.1 g |
| benzalkonium chloride | 0.005 g |
| sodium edetate | 0.01 g |
| sodium hydroxide | q.s. |
| sterile purified water | q.s. |
| total | 100 ml (pH 6.0) |

Formulation 8

| bunazosin hydrochloride | 0.5 g |
| boric acid | 0.5 g |
| conc. glycerol | 2.0 g |
| sodium hydroxide | q.s. |
| sterile purified water | q.s. |
| total | 100 ml (pH 5.5) |

Formulation 9

| bunazosin hydrochloride | 0.1 g |
| boric acid | 1.24 g |
| sodium borate | 0.1 g |
| conc. glycerol | 0.3 g |
| benzalkonium chloride | 0.005 g |
| sodium hydroxide | q.s. |
| dilute hydrochloric acid | q.s. |
| sterile purified water | q.s. |
| total | 100 ml (pH 6.0) |

STABILITY TEST

The photostability of ophthalmic solutions containing bunazosin hydrochloride as a typical drug substance was examined.

EXPERIMENTAL METHOD

The ophthalmic solution of the formulation 1 put in a polypropylene eye dropper bottle was exposed to light at 3000 luxes for 200 hours and the charge of color was examined.

As references, the following two ophthalmic solutions were prepared and compared with the ophthalmic solution of the formulation 1.

Reference 1

| bunazosin hydrochloride | 0.1 g |
| boric acid | 1.24 g |
| benzalkonium chloride | 0.005 g |
| sodium hydroxide | q.s. |
| sterile purified water | q.s. |
| total | 100 ml |

Reference 2

| bunazosin hydrochloride | 0.1 g |
| conc. glycerol | 0.3 g |
| benzalkonium chloride | 0.005 g |
| sodium hydroxide | q.s. |
| sterile purified water | q.s. |
| total | 100 ml |

EXPERIMENTAL RESULT

Table 1 shows the observation result before and after the exposure to light.

TABLE 1

| | before exposure | after exposure |
|---|---|---|
| Formulation 1 | colorless | colorless |
| Reference 1 | colorless | light red |
| Reference 2 | colorless | light red |

As shown in Table 1, the colors of the ophthalmic solutions adding boric acid ( Reference 1 ) and conc. glycerol ( Reference 2 ) were changed from colorless to light red by decomposition by light. On the other hand, coloration was not observed in the ophthalmic solution of the Formulation 1 combining boric acid and conc. glycerol, and a prevention of decomposition by light was attained. When bunazosin hydrochloride was excluded from formulation 1, no influence of light was observed.

As the result of the experiment, we found that the photostability of the ophthalmic solutions could be attained by combining polyhydric alcohol and boric acid, and/or sodium borate, while the addition of boric acid or polyhydric alcohol without the combination each other was not effective on photostability.

UTILITY IN AN INDUSTRY

By this invention, unstable drug substances against light can be easily applicable to ophthalmic solutions by combining polyhydric alcohol and boric acid, and/or sodium borate.

What we claim is:

1. A photostabilizing method which comprises adding 0.1 to 2 g/100 ml of glycerol and 0.5 to 2.5 g/100 ml of boric acid, to an ophthalmic solution containing a drug substance which is unstable against light, the total amount of the glycerol and the boric acid compound being 1.5 to 3 g/100 ml.

2. The method as in claim 1, wherein the drug substance is selected from the group consisting of bunazosin, prazosin, terazosin, epinephrine, phenylephrine and pharmaceutically acceptable salts thereof, and the polyhydric alcohol is selected from the group consisting of glycerol, polyethylene glycol, propylene glycol, mannitol and glucose.

3. The method as in claim 2, wherein the pH of the ophthalmic solution is 4.5 to 8.

4. The method as in claim 3, wherein the drug substance is bunazosin hydrochloride.

5. The ophthalmic solution as in claim 1, wherein the total amount of the glycerol and the boric acid is 1.5 to 2.5 g/100 ml.

6. The photostabilizing method as in claim 1, wherein the boric acid and the glycerol are in amounts selected from the group consisting of
   (a) 1 g/100 ml of boric acid and 0.5 g/100 ml of glycerol;
   (b) 2 g/100 ml of boric acid and 0.1 g/100 ml of glycerol; and
   (c) 0.5 g/100 ml of boric acid and 2 g/100 ml of glycerol.

7. An improved ophthalmic solution containing a drug substance which is unstable against light, the improvement comprising said ophthalmic solution further containing 0.1 to 2 g/100 ml of glycerol and 0.5 to 2.5 g/100 ml of boric acid, the total amount of the glycerol and the boric acid being 1.5 to 3 g/100 ml, to form a photostable ophthalmic solution.

8. The ophthalmic solution as in claim 7, wherein the drug substance is a compound which has an aromatic ring substituted by hydroxy, lower alkoxy, primary or secondary amine, or salts thereof.

9. The ophthalmic solution as in claim 7, wherein the drug substance is bunazosin hydrochloride.

10. The ophthalmic solution as in claim 7, wherein the drug substance is selected from the group consisting of bunzason, prazosin, terazosin, epinephrine, phenylephrine and pharmaceutically acceptable salts thereof, and the polyhydric alcohol is selected from the group consisting of glycerol, polyethylene glycol, propylene glycol, mannitol and glucose.

11. The ophthalmic solution as in claim 10, wherein the pH of the ophthalmic solution is 4.5 to 8.

12. The ophthalmic solution as in claim 11, wherein the drug substance is bunazosin hydrochloride.

13. The ophthalmic solution as in claim 12, consisting essentially of bunazosin hydrochloride, boric acid, glycerol, benzalkonium chloride, sodium hydroxide and water.

14. The ophthalmic solution as in claim 7, wherein the total amount of the glycerol and the boric acid is 1.5 to 2.5 g/100 ml.

15. The ophthalmic solution as in claim 7, wherein the boric acid and the glycerol are in amounts selected from the group consisting of
   (a) 1 g/100 ml of boric acid and 0.5 g/100 ml of glycerol;
   (b) 2 g/100 ml of boric acid and 0.1 g/100 ml of glycerol;
   (c) 0.5 g/100 ml of boric acid and 2 g/100 ml of glycerol.

16. A photostabilizing method which comprises adding a photostabilizing effective amount of 0.3 to 2 g/100 ml of glycerol and 0.5 to 2 g/100 ml of boric acid to an ophthalmic solution containing bunazosin hydrochloride, which is unstable against light, the total amount of the glycerol and the boric acid being 1.5 to 3 g/100 ml.

17. The ophthalmic solution as in claim 16, wherein the total amount of the boric acid and the glycerol is 1.5 to 2.5 g/100 ml.

18. An improved ophthalmic solution comprising an ophthalmic solution containing bunazosin hydrochloride which is unstable against light, the improvement comprising said ophthalmic solution further containing a photostabilizing effective amount of 0.3 to 2 g/100 ml of glycerol and 0.5 to 2 g/100 ml of boric acid, wherein the total amount of the glycerol and the boric acid is 1.5 to 3 g/100 ml, to form a photostable ophthalmic solution.

19. The ophthalmic solution as in claim 18, wherein the total amount of the boric acid and the glycerol is 1.5 to 2.5 g/100 ml.

* * * * *